US011089668B2

(12) United States Patent
Trutwig et al.

(10) Patent No.: US 11,089,668 B2
(45) Date of Patent: Aug. 10, 2021

(54) DEVICE FOR TREATING A SURFACE WITH A DIELECTRIC BARRIER PLASMA

(71) Applicant: CINOGY GMBH, Duderstadt (DE)

(72) Inventors: Leonhard Trutwig, Duderstadt/Gerblingerode (DE); Mirko Hahnl, Berlingerode (DE); Karl-Otto Storck, Duderstadt (DE); Dirk Wandke, Heilbad Heiligenstadt (DE); Matthias Kopp, Gieboldehausen (DE)

(73) Assignee: Cinogy GmbH, Duderstadt (DE)

( * ) Notice: Subject to any disclaimer, the term of this patent is extended or adjusted under 35 U.S.C. 154(b) by 448 days.

(21) Appl. No.: 16/065,993

(22) PCT Filed: Dec. 6, 2016

(86) PCT No.: PCT/DE2016/100591
§ 371 (c)(1),
(2) Date: Jun. 25, 2018

(87) PCT Pub. No.: WO2017/121421
PCT Pub. Date: Jul. 20, 2017

(65) Prior Publication Data
US 2019/0014651 A1 Jan. 10, 2019

(30) Foreign Application Priority Data
Jan. 13, 2016 (DE) .......................... 102016100466.9

(51) Int. Cl.
*H05H 1/24* (2006.01)
*A61B 18/14* (2006.01)
(Continued)

(52) U.S. Cl.
CPC ......... *H05H 1/2406* (2013.01); *A61B 18/042* (2013.01); *A61B 18/149* (2013.01);
(Continued)

(58) Field of Classification Search
CPC ................ A61B 18/042; A61B 18/149; A61B 2018/147; A61B 18/00–28;
(Continued)

(56) References Cited

U.S. PATENT DOCUMENTS

| 5,395,363 A | 3/1995 | Billings et al. |
| 5,925,040 A | 7/1999 | Nardella et al. |

(Continued)

FOREIGN PATENT DOCUMENTS

| DE | 102007030915 A1 | 1/2009 |
| DE | 102009060627 A1 | 6/2011 |

(Continued)

*Primary Examiner* — Joseph A Stoklosa
*Assistant Examiner* — Adam J Avigan
(74) *Attorney, Agent, or Firm* — W & C IP (57) ABSTRACT

A device for treating a surface with a dielectric barrier plasma, wherein the surface functions as a counterelectrode, has an electrically insulating housing and a housing head. A rotatable electrode connected to a high-voltage feed line is shielded by a dielectric and protrudes out of the housing head. The configuration has fundamentally unrestricted movement of the electrode over the surface to be treated in that the electrode has rotary bearing elements which are arranged in a center axis and a rotation axis is at an angle to the center axis.

10 Claims, 8 Drawing Sheets

(51) Int. Cl.
*A61B 18/04* (2006.01)
*A61N 1/44* (2006.01)
*A61B 18/00* (2006.01)
*A61L 2/00* (2006.01)
*A61L 2/14* (2006.01)
*B08B 7/00* (2006.01)

(52) U.S. Cl.
CPC ............ *A61L 2/0011* (2013.01); *A61L 2/0029* (2013.01); *A61L 2/14* (2013.01); *A61N 1/44* (2013.01); *A61B 2018/00452* (2013.01); *A61B 2018/147* (2013.01); *A61L 2202/11* (2013.01); *B08B 7/0035* (2013.01); *H05H 2001/2412* (2013.01); *H05H 2001/2418* (2013.01); *H05H 2277/10* (2013.01)

(58) Field of Classification Search
CPC ....... A61B 2018/00005–266; A61B 18/00583; A61B 18/1206; A61B 2018/00452; A61B 2018/0047; A61N 1/44; A61N 1/328; A61N 5/0616; A61N 2005/0644; H05H 1/2406; H05H 2001/2412; H05H 2001/2418; H05H 2277/10; H05H 2245/122; H05H 2240/20; H05H 2245/1225; H05H 2001/2431; H05H 2245/123; A61F 7/00–123; A61F 2007/0001–126; A61H 15/00–02; A61H 2015/0007–0071
See application file for complete search history.

(56) References Cited

U.S. PATENT DOCUMENTS

| | | | |
|---|---|---|---|
| 2008/0183167 | A1 | 7/2008 | Britva et al. |
| 2011/0087141 | A1* | 4/2011 | Wagy ................. A61H 15/0085 |
| | | | 601/137 |
| 2012/0022532 | A1 | 1/2012 | Garrison |

FOREIGN PATENT DOCUMENTS

| | | | | |
|---|---|---|---|---|
| DE | 102012103470 A1 | 10/2013 | | |
| DE | 102013000440 A1 * | 7/2014 | ........ | H01J 37/32348 |
| DE | 102013000440 B4 | 7/2014 | | |
| DE | 102013019058 A1 | 5/2015 | | |
| KR | 20110002210 A * | 1/2011 | | |
| KR | 20110002210 A | 1/2011 | | |
| WO | WO-2013156352 A2 * | 10/2013 | ........... | H05H 1/2406 |

* cited by examiner

DEVICE FOR TREATING A SURFACE WITH A DIELECTRIC BARRIER PLASMA

CROSS-REFERENCE TO RELATED APPLICATIONS

This application is a Rule 371 filing from PCT/DE2016/100591 filed Dec. 6, 2016, and that application claims priority to German Application 10 2016 100 466.9 filed Jan. 13, 2016.

FIELD OF THE INVENTION

The invention relates to a device for treating a surface with a dielectric barrier plasma, wherein the surface functions as a counter electrode, having an electrically insulating housing, which is formed from a housing body and a housing head and in which is situated a high voltage feed line and a bearing arrangement for an electrode, which is connected to the high voltage feed line, with a dielectric which shields the electrode from the surface, wherein the electrode is rotatably mounted in the housing head and protrudes out of the housing head by way of a surface portion which is covered by the dielectric.

BACKGROUND

It has been known for a long time that surfaces of bodies are able to be influenced advantageously for certain applications by a plasma treatment. Thus, it is possible to facilitate the application of paints or other chemical treatment agents on a surface which would not be workable in the desired form without a corresponding preparation. The originally provided realization of a hot plasma on such surfaces presupposes costly apparatuses and safety regulations which have to be strictly adhered to as operating personnel have to be carefully shielded from the high voltage that generates the plasma and from the hot plasma itself.

It has been shown that it is possible to treat surfaces with a dielectric barrier plasma which is certainly also generated with a high voltage, in particular an alternating high voltage, but as cold plasma does not have to be kept away from operating personnel. In particular, it has been shown that surfaces of living bodies, that is to say skin and wound surfaces, are also able to be treated in an advantageous manner with a dielectric barrier plasma because the plasma enables, for example, reliable disinfection even in regions of the surface that are difficult to access and, over and above this, can prepare the surface of the skin for the receiving of nurturing or healing substances and can have a positive effect on the wound healing in general, for example by increasing the microcirculation in the tissue.

It has been shown that a secure and effective realization of the plasma is possible as a result of the body associated with the surface to be treated being used as a counter electrode (so-called "floating electrode"). The result for the treatment device is that it comprises just one electrode—which carries the high voltage—and does not require a dedicated counter electrode.

A device for treating a surface with a dielectric barrier plasma is disclosed in DE 10 2007 030 915 A1. An elongated electrode with a cylindrical cross section and a rounded end face, in this case, is surrounded by a correspondingly realized dielectric. A surface, for example a part of the skin, can be treated with the shell surface of the dielectric. Uniform treatment of a larger surface is not provided with this type of a device.

DE 10 2009 060 627 provides a flat electrode arrangement for the treatment of larger parts of the skin, in the case of said electrode arrangement a flat electrode is shielded from a surface to be treated, in particular a surface of the skin, by a flat dielectric. To adapt to irregular surfaces, both the electrode and the dielectric are realized in a flexible manner. Such a flat electrode can be placed onto the surface to be treated, the dielectric being realized in a structured manner in order to leave an air gap between the skin and the dielectric in which the plasma discharge is able to take place when the surface to be treated is used as a counter electrode. A disadvantage of said arrangement is the large surface area of the electrode arrangement which is preferably usable on a stationary device and, over and above this, only enables the treatment of strongly curved surfaces in a limited manner.

In order to enable a device for treating a surface with a dielectric barrier plasma, by way of which, with simple handling, the plasma treatment of both strongly curved surfaces and larger surface areas is possible, devices have been proposed which are easily guidable over the surface. According to DE 10 2012 103 470 A1, treatment of a surface with a dielectric barrier plasma is to be effected by means of a ball-shaped electrode which is able to rotate freely in a housing. The coupling of an alternating high voltage is to be effected capacitively by means of a coupling electrode. This results in the current flow to the ball-shaped electrode already being dielectrically impeded. When the electrode rests on the surface to be treated without any dielectric shielding, a ring-shaped region, in which the dielectric barrier plasma is able to be realized, is consequently realized about the punctiform contact between the ball and the surface to be treated. When, however, according to another exemplary embodiment, the ball-shaped electrode is encased with a dielectric layer, it is no longer possible, with sensible expenditure, to realize plasma on the surface. The treatment of conductive surfaces, where the shielding of the ball-shaped electrode is necessary to avoid arc discharging, is consequently not able to be carried out sensibly with the disclosed device.

A device of the type mentioned in the introduction is disclosed in DE 10 2013 019 058 A1. In an advantageous manner, the electrode in the form of a rotatable ball is situated in a housing head which is connected in a latching manner to a housing body which is realized as a handle. The high voltage feed is situated in the housing body. The contacting of the electrode with the high voltage feed is effected by the housing head comprising a connecting pin which is connected to the electrode and, with the housing in the mounted state, protrudes into a suitable guide channel in the handle part and is connectable there to the high voltage feed. The ball-shaped electrode is connected, in turn, to the connecting pin by means of a conductor loop such that the ball, which protrudes out of an end-face opening of the housing head by way of a ball section surface, is only rotatable in a restricted manner in each case. To protect the connection between the conductor loop and the ball, the rotation of the electrode is delimited mechanically by means of stops. The surface of the ball is almost completely provided with a dielectric such that the ball-shaped electrode, in the region in which it is able to protrude out of the housing head, is covered by the dielectric in every rotational position. The dielectric comprises a structured surface in the form of numerous nubs which realize air gaps between them in which the plasma is able to be generated by the high voltage of the electrode even when the dielectric of the electrode rests—in a substantially punctiform manner—on the surface to be treated. In practice, said device completely fulfills the treatment function by the plasma. However, occasionally seen as a disadvantage is that the electrode is only restrictedly rotatable such that the guiding of the electrode over the surface to be treated is also determined as a result of the ball-shaped electrode no longer being able to rotate along a treatment path, such that the treatment path has to be angled by at least 90°. A back and forth movement is frequently also carried out in this case.

It is also expedient in the case of the device according to the invention when the dielectric covering the electrode comprises a structured surface, the plasma is able to be realized when abutting against the surface to be treated.

SUMMARY

The object underlying the invention is accordingly to realize a device of the type mentioned in the introduction such that the guiding of the electrode over the surface to be treated is not impaired by a delimited rotation angle of the electrode, wherein simple galvanic contacting of the electrode with the high voltage is to be maintained.

To achieve said object, a device of the type mentioned in the introduction is characterized according to the invention in that the electrode comprises pivot bearing elements which are arranged in a center axis and by way of which, in conjunction with pivot bearing elements in the housing head, it is mounted so as to rotate about the center axis and is connected to the high voltage feed line, and in that the housing head is connected to the housing body so as to be rotatable about a rotational axis, which is at an angle, preferably perpendicular, to the center axis, and is provided with a contact arrangement for maintaining an electric connection during the rotation.

The device according to the invention enables free movement over the surface to be treated as a result of the electrode itself only being rotatable about one single rotational axis, the housing head which supports the electrode, however, itself being able to be rotated about a rotational axis which is at an angle, preferably perpendicular, thereto. When the two rotations are set up in an unrestricted manner, each treatment path is able to be realized on the surface to be treated. Within the framework of the invention, however, it is also possible to delimit at least one of the rotations for structural reasons, as a result of which there can be a small restriction in the treatment paths, however, in addition, a large amount of mobility of the electrode over the surface to be treated can be ensured with faultless contacting of the electrode. In the case of the device according to the invention, the contacting with the high voltage is maintained during the rotation about the respective rotational axis, preferably at least one pivot bearing enabling unrestricted rotation. In an embodiment of the invention, the bearing arrangement of the electrode is realized in any case in the housing head such that the electrode is rotatable with the dielectric in an unrestricted manner about the rotational axis. For this purpose, the pivot bearing elements of the electrode and of the housing head are preferably formed by axial projections and corresponding receiving means which are formed from electrically conducting material. The axial projections can be situated, in this case, on the electrode or on the housing head, the associated receiving means being arranged on the corresponding other part. In a structurally simple embodiment, the axial projections are situated on the electrically conducting electrode. The electrode is also preferably situated in the housing head and protrudes out of an opening of the housing head simply with a surface portion which is completely covered by the dielectric.

As the electrode rotates about a fixed axis, it can have the form of a roller, the basic design of which is disclosed in DE 10 2013 000 440 B4. The surface portion, which preferably protrudes out of the opening of the housing head, can be realized as a straight cylinder portion or as a two-dimensional arch. The straight cylinder portion results in a linear abutment of the surface portion against the surface to be treated, whereas the two-dimensional arch leads to a punctiform abutment when the surface to be treated can be comprehended as a plane.

The electrode can be realized in a flexible manner irrespective of its form by consisting, for example, of a spring-elastic material which can be formed from a wound wire or wire mesh or expanded metal grating, and is covered by a flexible dielectric as is also described in principle in DE 10 2013 000 440 B4. The electrode is able to be adapted as a result to possible irregularities of the surface to be treated.

The rotatable bearing arrangement of the housing head in the housing body is effected in an expedient manner by means of insulating plastic parts of the housing body, on the one hand, and of the housing head on the other hand. The advantage of said realization is that the housing head is fastenable on the housing body by means of a latching connection which is realizable in a slightly rotationally symmetrical manner as a result of correspondingly formed plastic parts such that the housing head is mounted so as to be rotatable about a fixed rotational axis relative to the housing body.

For the production of the electric connection between the high voltage feed line of the housing body and the electrode of the housing head, it is expedient in a structurally simple realization when the pivot bearing elements of the housing head are connected to an electrically conducting pin which, with the housing in the mounted state, protrudes rotatably in the housing body by way of a free end into the contact arrangement which carries the high voltage. In this case, it is expedient when the electrically conducting cylindrical pin is surrounded in front of the free end with a plastic sleeve of the housing head which is realized so as to be rotatably insertable into a receiving means of the housing body, wherein the push-in distance of the plastic sleeve into the receiving means is longer than the contact section between the free end of the electrically conducting cylindrical pin and the contact arrangement. The contact arrangement, in this case, can be formed in an expedient manner by an electrically conducting sleeve which, with radial pre-tensioning, abuts against the free end of the electrically conducting pin at least over a defined axial length.

It is also expedient in the case of the device according to the invention when the dielectric which covers the electrode comprises a structured surface which ensures the realization of air gaps, in which the plasma is able to be realized, when abutting against the surface to be treated.

DESCRIPTION OF THE DRAWINGS

A pluggable realization of the housing head in the housing body, where a latching connection is produced, enables the realization of a head part of the device which is easily able to be replaced after the treatment, in order thus to serve as a disposable part or as a structural element which is to be easily disinfected in a device. In particular as a single-use component, it is important for the head part to be designed in a simple and cost-efficient manner. Such a design is to be found in the following description of an exemplary embodiment of the invention which is shown in the drawing, in which.

DETAILED DESCRIPTION

Figure 1:
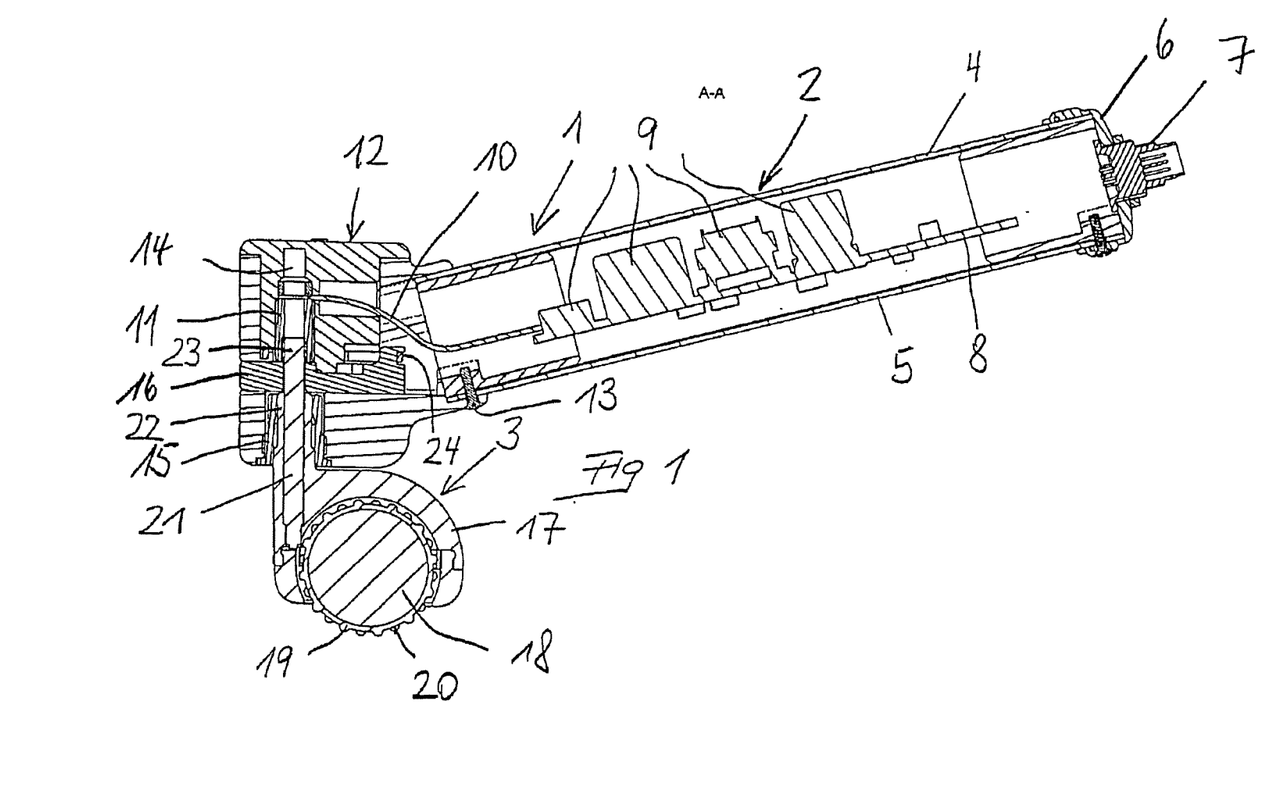
FIG. 1 shows a vertical section through an exemplary embodiment of a device according to the invention with a housing head inserted into the housing body.

The device shown in FIG. 1 for treating a surface with a dielectric barrier plasma comprises a housing 1 which consists of a handle part 2 and a head part 3 which are realized so as to be easily separable from one another, such that the head part 3 is mountable on the handle part 2 so as to be replaceable in order to be replaced by a new head part 3 after a treatment. This also enables, in particular, the realization of a head part which is disinfected or disposed of after the treatment. Consequently, the device according to the invention is suitable, in particular, for treating the skin or a wound surface of a living body. The treatment carried out in this case can be of a medical or cosmetic type.

The handle part comprises a housing body 4 which includes an elongated cylindrical wall portion 5, by means of which the handle part 2 is able to be gripped by a hand. The cylindrical wall portion is closed at one end face, which points away from the head part 3, by a cap 6 into which a plug connector 7, which is realized for the connection of a power supply cable, is inserted. Instead of the plug connector 7, the cap 6 can also comprise a cable duct for a power supply cable. Inside the housing body 4, in the region of the cylindrical wall portion 5, is situated a circuit board 8 with assemblies 9 arranged thereon, by way of which a high voltage is generated from the supplied power voltage, which can be mains voltage, using conventional technology. To this end, for example the usual mains AC voltage can be rectified and chopped (preferably at a high frequency) and stepped up to the high voltage. At the output of the assemblies 9, there is then an alternating high voltage which is carried to a contacting element 11 by means of an internal conductor 10. In a similar technique, the supply voltage can also be removed from a battery or an accumulator and supplied to the chopper. Batteries or accumulators can be accommodated in the handle part 2 such that a cable duct or a plug 7 is not required.

In an alternative embodiment, a high voltage can already be supplied through the cap 6 preferably by means of a cable duct, as a result of which the generation of the high voltage in the handle part 2 can be omitted. For reasons of safety, however, the supply of a usual mains voltage and the generation of the high voltage required for the plasma treatment in the housing 1 is preferred.

The contacting element 11 is situated in an end housing part 12 of the housing body 4 which is fixedly mounted on the end of the cylindrical wall portion 5 opposite the cap 6, for example by way of at least one screw 13. The end housing part 12 comprises a blind bore 14 which is open toward the head part 3, the axis of which, with an imaginary longitudinal axis of the cylindrical wall portion 5, forms an angle which is somewhat greater than 90° and lies preferably between 100 and 120° such that the handle part 3 extends upward somewhat toward the free end when the blind bore 14, for the treatment of the surface, is perpendicular to the surface.

The contacting element 11 in the form of a cylindrical sleeve is inserted into the blind bore 14. In addition, an inserted plastic sleeve part 15, which is connected fixedly, for example as a result of bonding, to the end housing part 12, is situated on the lower end of the blind bore 14. Between the contacting element 11 and the plastic sleeve part 15, the end housing part 12 comprises a recess into which is inserted a cross slider 16, which comprises a passage opening which is aligned with the blind bore 14 in the state shown in FIG. 1.

It can additionally be seen from FIG. 1 that in the mounted state shown, the head part 3 comprises a head housing 17, in which a ball-shaped electrode 18 in the exemplary embodiment shown is rotatably mounted, as will be explained in more detail below. The surface of the electrode 18 is covered by a dielectric 19, the outer surface of which comprises a structuring in the form of numerous nubs 20. An electrically conducting cylindrical pin 21, which is guided through a projection of the head housing 17 which forms a plastic sleeve 22 and protrudes out of the plastic sleeve by way of a free end 23, is mounted in the head housing 17. The free end 23 of the electrically conducting cylindrical pin 21, which is not covered by the plastic sleeve 22, protrudes into the sleeve forming the contacting element 11 in the end housing part 12, as a result of which the high voltage transmitted to the contacting element 11 is transmitted to the electrically conducting cylindrical pin 21. Said electrically conducting pin is electrically connected to the electrode 18 in a manner which is to be explained in more detail below, as a result of which the high voltage required for generating the plasma passes to the electrode 18.

Figure 2:
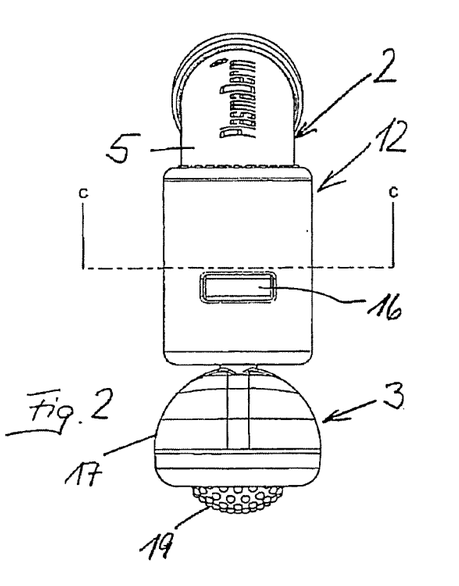
FIG. 2 shows a view of an end face of the device according to FIG. 1.

The cylindrical pin 21, in this case, runs through an opening of the cross slider 16 which is pre-tensioned radially outward, that is to say away from the cylindrical wall portion 5, by means of a spring 24. The introduction of the cylindrical pin 21 into the blind bore 14 up to the contacting element 11 is consequently only successful when the cross slider 16 is slid against the force of the spring 24 into the position shown in FIG. 1. If the head part 3 is removed out of the handle part 2, the spring 24 pulls the cross slider 16 outward, as a result of which the blind bore 14 is blocked by a solid portion of the cross slider 16 such that access from the open end through the blind bore 14 to the contacting element 11 carrying the high voltage is not possible. In said position, the cross slider 16 protrudes out of the end housing part 12 in the manner of a button. The view in FIG. 2 clarifies the position of the cross slider 16 in the end housing part and the position of the head part 3 inserted into the handle part 2, where a surface portion of the electrode 18 protrudes downward out of the opening of the head housing 17 with the dielectric which surrounds it. The surface portion which protrudes out of the opening, in this case, lies clearly below the largest diameter of the electrode 18, that is to say clearly below the rotational axis of the electrode 18.

Figure 3:
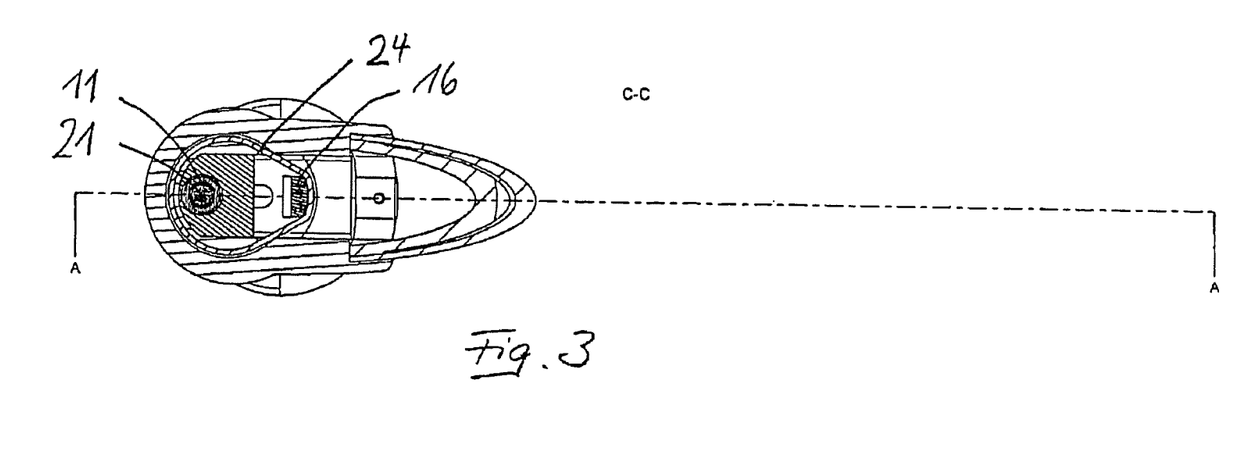
FIG. 3 shows a horizontal section along the line C-C in FIG. 2.

FIG. 3 shows the form of the spring 24 used here which is guided as a closed flat spiral spring in the end housing part 12 and wraps around an upwardly protruding projection of the cross slider 16 toward the cylindrical wall portion 5 of the housing body 4. The flat spiral spring 24, in this case, is realized in an elastic manner and in the tensioned state shown in FIG. 1 deforms elastically from an initial circular ring shape, as a result of which the outwardly directed pre-tensioning is generated, pulling the cross slider under the effect of the spring 24 into a position closing the blind bore 14 when the cylindrical pin 23 is pulled out of the blind bore 14.

It can be seen from FIG. 1 that the plastic sleeve 22 of the head housing 17 and the plastic sleeve part 15 surrounding it in the inserted state are formed in a complementary manner in order to produce a latching connection between the housing body 4 and the housing head 17, as a result of which the head part 3 is realized so as to be easily removable from the handle part 2 such that it is able to be easily replaced.

Figure 4:
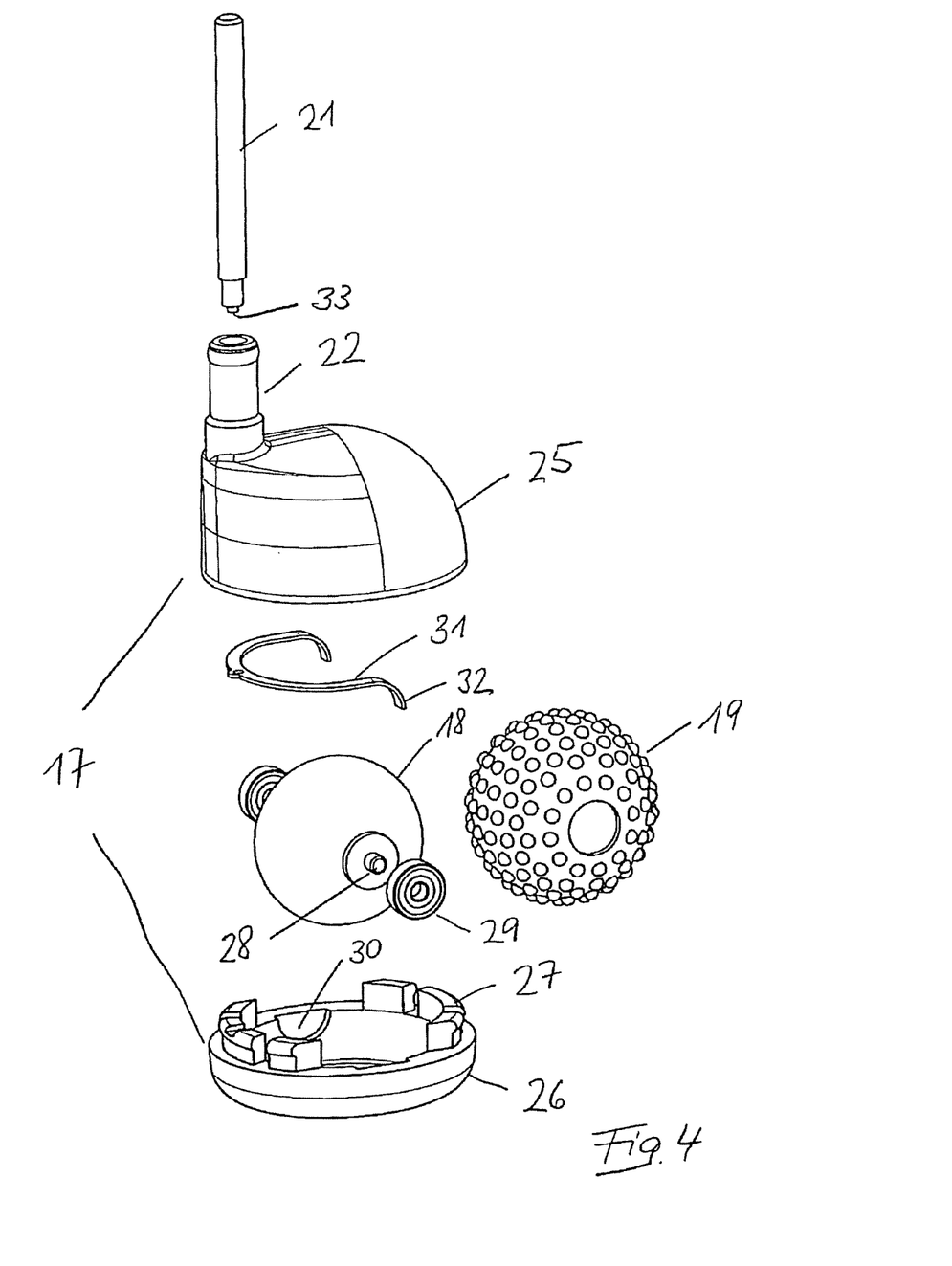
FIG. 4 shows an exploded representation of the housing head.

FIG. 4 shows an exploded representation of the head part 3 and it can be seen that the housing head 17 is realized with two parts and consists of an upper flattened dome part 25 and a lower locking ring 26 which are connectable together by means of latching lugs 27. The butt joint between the flattened dome part 25 and the locking ring 26 is situated at the height of the largest diameter of the electrode 18 inserted into the housing head 17 with the dielectric 19 surrounding it. The locking ring 26 continues the flattened dome shape downward and consequently forms a flattened dome portion ring, by means of which the electrode is secured against falling out in the housing head 17.

Figure 5:
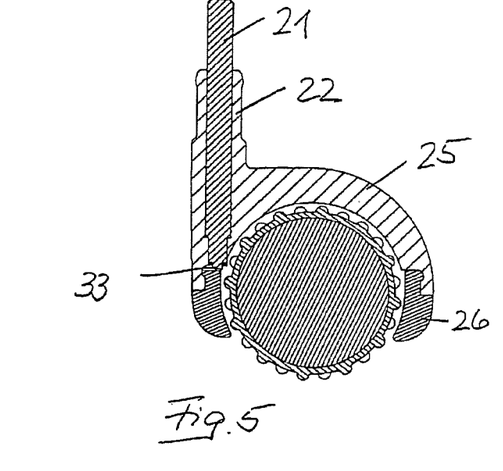
FIG. 5 shows a vertical section through the housing head according to FIG. 4.
Figure 6:
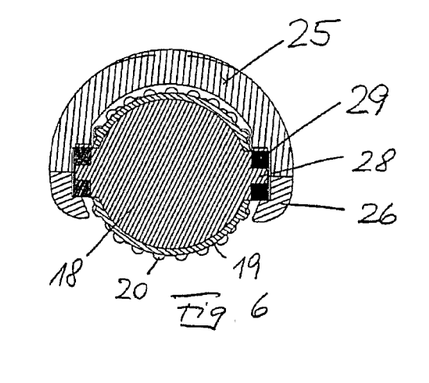
FIG. 6 shows a vertical section through the housing head rotated by 90°.
Figure 7:
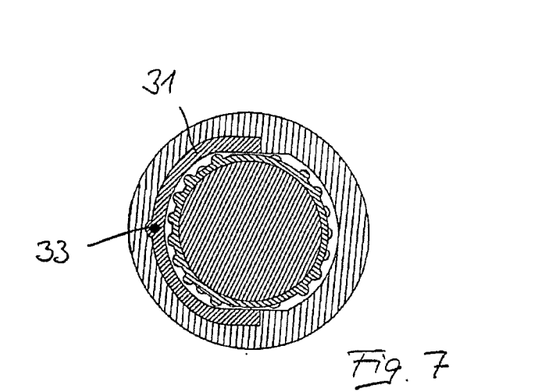
FIG. 7 shows a horizontal section through the housing head.

For the rotatable bearing arrangement of the electrode 18, said electrode is provided with diametrically opposite axial projections 28 which are insertable non-rotatably into an inner ring of a ball bearing 29. The outer ring of the ball bearing 29 is mounted non-rotatably in the housing head 17, for which corresponding semicircular recesses 30, which are put together to form a ring-shaped recess which receives the outer ring of the ball bearing 29, are provided on the inner wall both in the locking ring 26 and in the flattened dome part 25 (not visible). The outer and inner ring and the balls of the ball bearing 29 rolling on the outer and inner ring consist of a conductive material, in particular steel, such that the outer ring of the ball bearing is connected conductively to the axial projections 28 of the electrode 18—and consequently to the electrode itself. A semicircular spring contact 31, in which rounded angled ends 32 rest on the outer rings of the ball bearing 29 under pre-tensioning, makes contact with the two outer rings of the ball bearings 29. The contact between the spring contact 31 and the electrically conducting cylindrical pin 21 is produced as a result of the electrically conducting pin 21 being realized on the lower end as a small bolt 33 with a reduced diameter which protrudes into a corresponding opening 34 and is connectable there in a conducting manner to the spring contact 31. The sectional representations of FIGS. 5, 6, and 7 clarify the design of the mounted housing head 7 with the electrode mounted therein.

Figure 8:
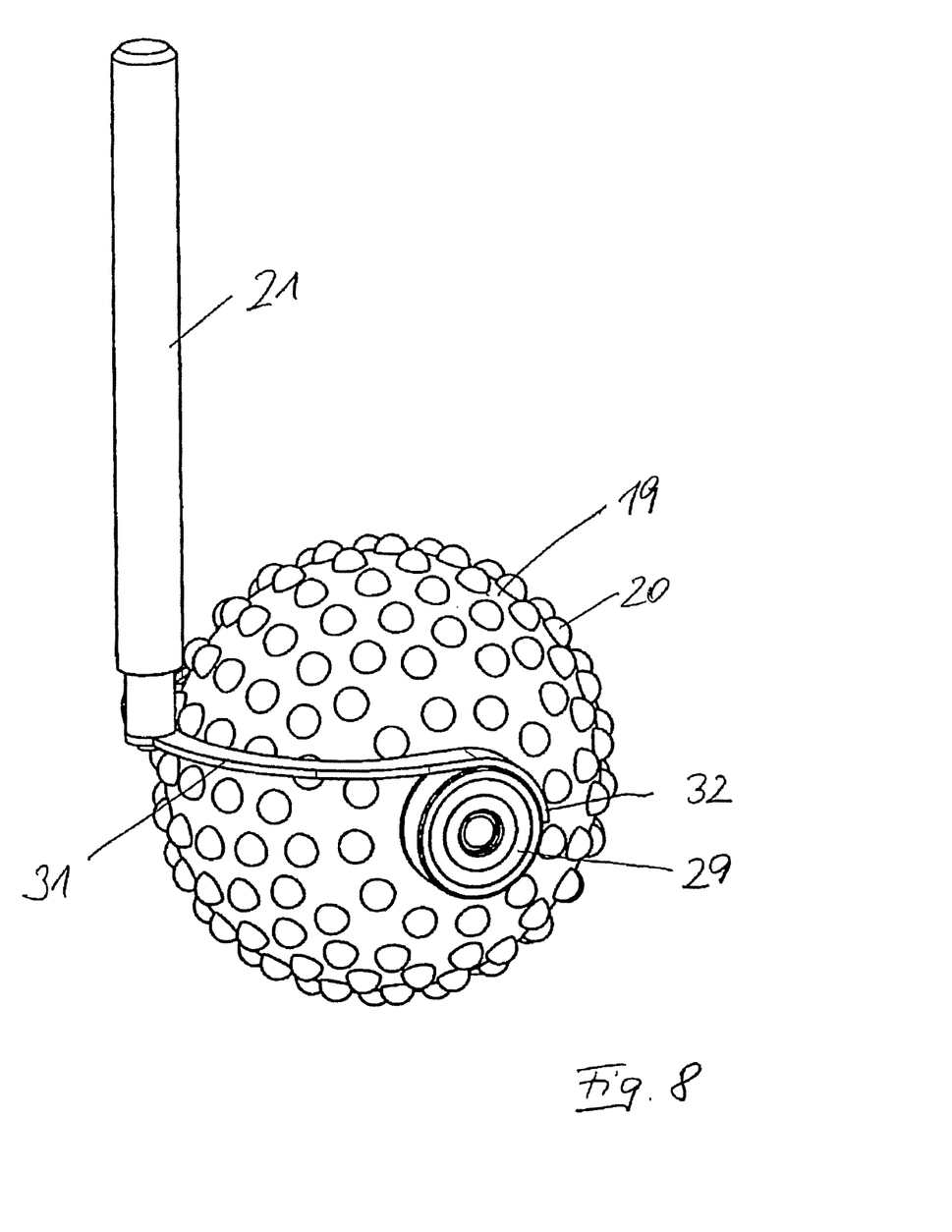
FIG. 8 shows a representation of the arrangement for contacting the electrode inside the housing head.

FIG. 8 shows the contacting system for the electrode in a separate representation without the supporting housing head 17. FIG. 8, in this case, clarifies that the axial projections 28 project into the interior of the ball bearing 29 through the dielectric 19 which surrounds the electrode 18. The live parts lying outside the dielectric 19, namely ball bearing 29, spring contact 31 and cylindrical pin 21, are covered in an insulating manner by the housing head 17. Consequently, it is important that only one surface portion lying clearly below the meridian of the ball protrudes out of the bottom of the housing head 17, as is made clear again in FIG. 9. It can additionally be seen in FIG. 9 that the plastic sleeve 22, which surrounds the electrically conducting cylindrical pin 21 below the free end 23 thereof, is realized with a latching groove 35 and a latching bead 36 which produce the latching connection which enables rotation about the center axis of the plastic sleeve 22 or of the cylindrical pin 21 with corresponding counter pieces in the plastic sleeve part 15 of the end housing part 12.

Figure 9:
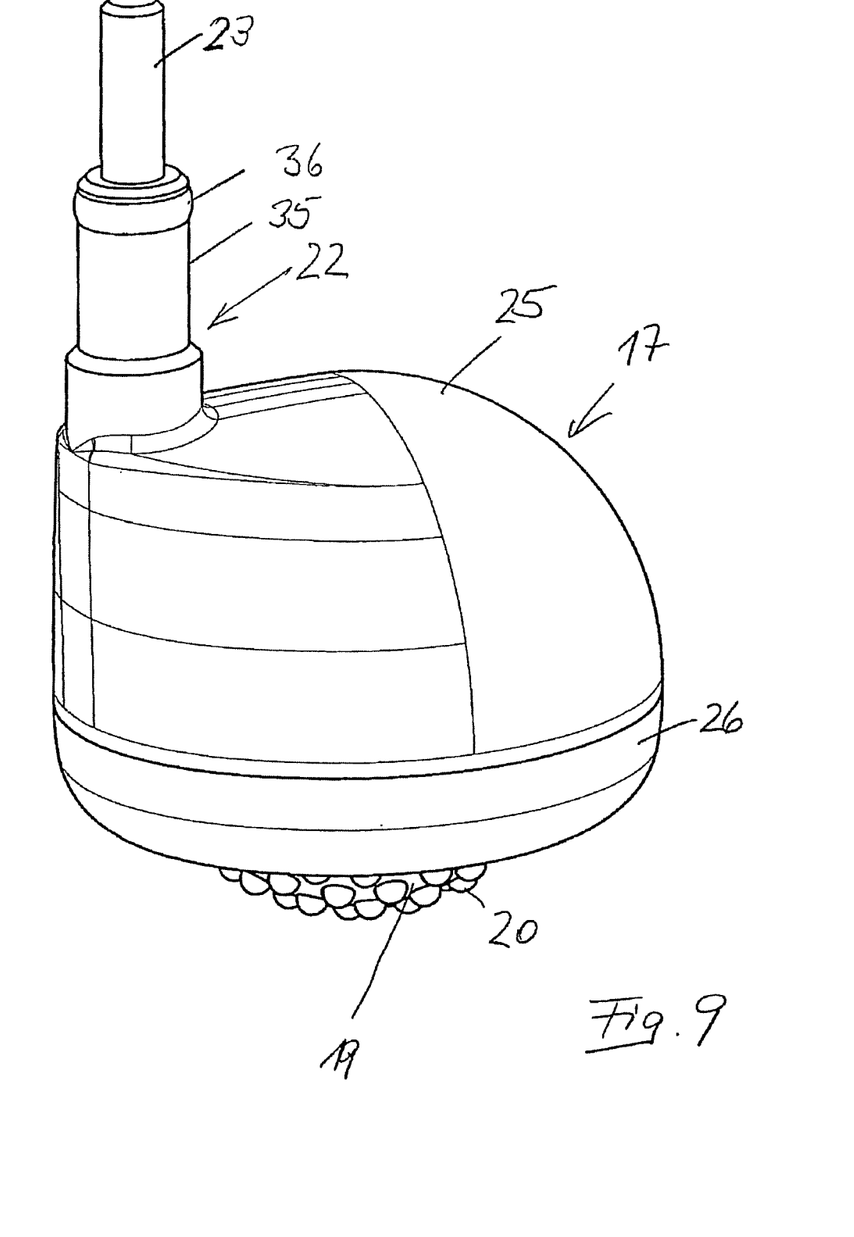
FIG. 9 shows a view of the head part of the device with the surface portion of the electrode protruding out of the housing head.

FIGS. 8 and 9 additionally clarify the embodiment of the surface of the dielectric 19, which is structured as a result of nubs 20, by means of which, even with the nub tips abutting against the surface to be treated, air gaps exist between the nubs 20, in which air gaps, on account of the high voltage supplied to the electrode 18, the dielectric barrier plasma can be realized as a counter electrode relative to the surface to be treated. However, the realization of the structured surface with nubs is not compulsory. It is equally possible to structure the surface in a different manner, for example with a grid structure, among other things, as air gaps closed off by the grid structure also enable plasma to be realized.

Figure 10:
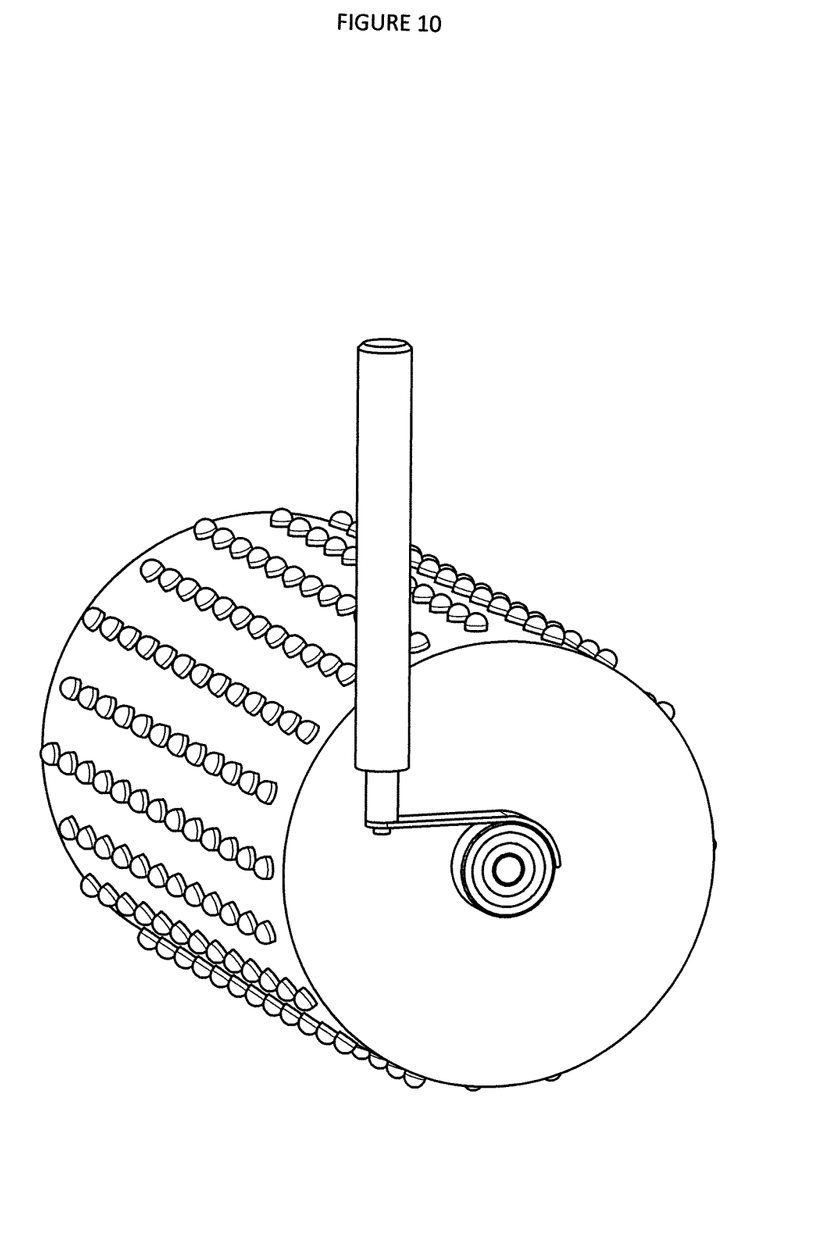
FIG. 10 shows a representation of the arrangement similar to FIG. 8 but where a straight cylinder is employed.

In addition, the description of the exemplary embodiment clarifies for the expert that the electrode 18 in no way has to be present in the form of a ball, as the electrode is rotatable only about the rotational axis which extends through the centers of the axial projections, such that for said rotation, a cylindrical electrode is also usable within the framework of the invention as is shown by example in FIG. 10. This can comprise a straight cylindrical shell surface or also a two-dimensionally arched surface portion. Insofar as the electrode protrudes out of a (slot-shaped) opening of the housing head 17 by way of only one surface portion, said surface portion preferably also lies below the largest horizontal width of the cylindrical electrode, that is to say clearly below the pivot bearing elements formed, for example, by axial projections 28. For the free movement according to the invention of the electrode 18 over the surface to be treated, it can be expedient not to choose the length of the roller too large in relation to the diameter.

The ratio of length to diameter can be chosen for this to be $\leq 2:1$, preferably $\leq 1.5:1$. This is in particular advantageous for a straight cylindrical and a slightly arched shell surface. A shell surface, the arch radius of which in the longitudinal direction of the roller is more than twice as large as the largest radial diameter of the roller perpendicular to the longitudinal direction, is deemed to be slightly arched.

In the exemplary embodiment shown, the rotational axes for the electrode 18, on the one hand, and for the housing head 17, on the other hand, are perpendicular to one another, such that where the position of the handle part 2 is unchanged as regards the angle to the surface to be treated, free movement is possible along a planar surface to be treated. If the axis of the pin forms an angle which deviates (slightly) from 90° with the rotational axis of the electrode 18, a movement along a funnel-shaped shell surface is exercised, which is also possible and a change in the position of the housing 1 can also be performed at any time especially by guiding the device manually at the handle part 2. As a rule, a perpendicular orientation of the two rotational axes with respect to one another will be advantageous.

The invention claimed is:

1. A device for treating a surface with a dielectric barrier plasma, wherein the surface functions as a counter electrode, comprising:

an electrically insulating housing which is formed from a housing body and a housing head;
a high voltage feed line situated in the housing;
an electrode;
a bearing arrangement for the electrode connected to the high voltage feed line;
a dielectric which shields the electrode from a surface, wherein the electrode is rotatably mounted in the housing head and protrudes out of the housing head by way of a surface portion which is covered by the dielectric,
wherein the electrode comprises pivot bearing elements which are arranged in a center axis,
wherein the housing head includes pivot bearing elements,
wherein the electrode is mounted, using the pivot bearing elements of the electrode in conjunction with the pivot bearing elements of the housing head, so as to rotate about the center axis,
wherein the electrode is connected to the high voltage feed line,
wherein the housing head is connected to the housing body so as to be rotatable about a rotational axis which is at an angle to the center axis; and
a contact arrangement connecting the housing head to the housing body for maintaining an electric connection during rotation formed by an electrically conducting sleeve and an electrically conducting pin, said electrically conducting pin being rotatably inserted into said electrically conducting sleeve for conducting the high voltage to the electrode.

2. The device as claimed in claim 1, wherein the electrode is rotatably mounted in a non-restricted manner in the housing head.

3. The device as claimed in claim 1 wherein the pivot bearing elements of the electrode and the pivot bearing elements of the housing head are formed by axial projections and corresponding receiving means produced from electrically conducting material.

4. The device as claimed in claim 3 wherein the surface portion is configured such that it protrudes out of the housing head when the electrode is rotated, and the surface portion comprises a two-dimensional arch for punctiform abutment against the surface to be treated.

5. The device as claimed in claim 1 wherein the surface portion is configured such that it protrudes out of the housing head when the electrode is rotated, and is in a form of a straight cylinder intersection for linear abutment against the surface to be treated.

6. The device as claimed in claim 1 wherein the electrode protrudes out of an opening of the housing head only by way of the surface portion.

7. The device as claimed in claim 1 wherein the housing head is rotatably mounted in a non-restricted manner in the housing body.

8. The device as claimed in claim 1 wherein the electrically conducting cylindrical pin protrudes in the housing body by way of a free end.

9. The device as claimed in claim 8, wherein the electrically conducting cylindrical pin is surrounded in front of the free end with a plastic sleeve of the housing head, wherein a push-in distance of the plastic sleeve into a receiving means of the housing body is longer than a contact section between the electrically conducting cylindrical pin and the electrically conducting sleeve of the contact arrangement.

10. The device as claimed in claim 1 wherein the housing head is fastened on the housing body by a latching connection.

* * * * *

UNITED STATES PATENT AND TRADEMARK OFFICE
CERTIFICATE OF CORRECTION

| | |
|---|---|
| PATENT NO. | : 11,089,668 B2 |
| APPLICATION NO. | : 16/065993 |
| DATED | : August 10, 2021 |
| INVENTOR(S) | : Trutwig et al. |

It is certified that error appears in the above-identified patent and that said Letters Patent is hereby corrected as shown below:

On the Title Page

Item (22) PCT Filed should read: Dec. 16, 2016

Signed and Sealed this
Third Day of May, 2022

Katherine Kelly Vidal
*Director of the United States Patent and Trademark Office*